United States Patent
Wik et al.

(10) Patent No.: US 10,524,771 B2
(45) Date of Patent: Jan. 7, 2020

(54) ORGAN RETRACTION DEVICE

(71) Applicant: Baxter International Inc., Deerfield, IL (US)

(72) Inventors: Patrick A. Wik, Lutherville, MD (US); Elizabeth A. Dovec, Lutherville, MD (US)

(73) Assignee: BAXTER INTERNATIONAL INC., Deerfield, IL (US)

(*) Notice: Subject to any disclaimer, the term of this patent is extended or adjusted under 35 U.S.C. 154(b) by 75 days.

(21) Appl. No.: 15/631,069

(22) Filed: Jun. 23, 2017

(65) Prior Publication Data
US 2018/0263613 A1 Sep. 20, 2018

Related U.S. Application Data

(60) Provisional application No. 62/471,405, filed on Mar. 15, 2017.

(51) Int. Cl.
*A61B 17/02* (2006.01)

(52) U.S. Cl.
CPC .................. *A61B 17/02* (2013.01)

(58) Field of Classification Search
CPC .............. A61B 17/02; A61B 17/0218; A61B 2017/0225
See application file for complete search history.

(56) References Cited

U.S. PATENT DOCUMENTS

| | | | | |
|---|---|---|---|---|
| 5,934,283 A | * | 8/1999 | Willem | A61F 2/0045 128/885 |
| 6,695,855 B1 | * | 2/2004 | Gaston | A61B 17/0469 600/29 |
| 7,981,023 B2 | * | 7/2011 | Nowlin | A61F 2/0045 600/30 |
| 2008/0081945 A1 | * | 4/2008 | Toso | A61F 2/0045 600/37 |
| 2009/0137877 A1 | * | 5/2009 | Minnelli | A61B 17/0218 600/204 |
| 2009/0171143 A1 | * | 7/2009 | Chu | A61B 17/0401 600/37 |
| 2009/0221868 A1 | * | 9/2009 | Evans | A61B 17/0401 600/37 |
| 2010/0174134 A1 | * | 7/2010 | Anderson | A61B 17/06109 600/37 |

* cited by examiner

*Primary Examiner* — Lynnsy M Summitt
*Assistant Examiner* — Tara Rose E Carter
(74) *Attorney, Agent, or Firm* — K&L Gates LLP

(57) ABSTRACT

A disclosed medical device may have a sling, a first needle coupled to a first end of the sling and a second needle coupled to the second end of the sling. The first needle may be coupled via a first suture having one point of attachment on the sling, and the second needle may be coupled via a second suture having two points of attachment on the sling. The sling may be used in laparoscopic surgeries and is intended to, if desired, be left in place during the procedure. The sling is further configured to allow a surgeon to visualize the full and proper surgical field by holding and retaining at least one organ.

9 Claims, 9 Drawing Sheets

ORGAN RETRACTION DEVICE

CLAIM OF PRIORITY

This application claims the priority of U.S. Ser. No. 62/471,405 filed on Mar. 15, 2017, the contents of which are fully incorporated herein by reference.

FIELD OF THE EMBODIMENTS

The field of the present invention and its embodiments relate to an organ laparoscopic retraction device, namely a liver retraction device. In particular, the embodiments describe an organ retractor that forms a "sling" to position the organ during laparoscopic surgery.

BACKGROUND OF THE EMBODIMENTS

Laparoscopic surgery, also called minimally invasive surgery, bandaid surgery, or keyhole surgery, is a modern surgical technique in which operations are performed through small incisions, usually 0.5-1.5 cm, located on the body of the patient.

There are a number of advantages for a patient who undergoes laparoscopic surgery rather than a traditional "open" procedure. Patient pain and hemorrhaging are reduced due to the smaller incisions utilized in laparoscopic type surgeries and recovery times are thus shorter.

Notwithstanding the above, minimally invasive surgery is still in its infancy. Throughout the past two decades numerous devices have been developed to enable safer and faster procedures, including anastomosis creating devices, energy sources, and superior surgical site imaging.

However, there are also a number of shortcomings of laparoscopic surgeries including but not limited to, a limited range of motion at the surgical site for the surgeon resulting in a loss of dexterity, poor depth perception as it relates to the surgical site, an inability to accurately judge how much force is being applied to tissue, and a lack of desired results as opposed to when the patient and surgical area can be opened up.

Additionally, retraction capabilities have been put aside and currently, organ laparoscopic retraction is based on standard laparoscopic tools. The evolution of laparoscopic surgery lends itself towards an era of minimizing the number of ports and shrinking the port size even further.

Thus, there is a need for an organ laparoscopic retractor, preferably for a liver, that may be inserted/removed through the port and positioned in the cavity throughout the procedure. The present invention and its embodiments meets and exceeds these objectives.

Various systems and methodologies are known in the art. However, their structure and means of operation are substantially different from the present disclosure. The other inventions fail to solve all the problems taught by the present disclosure. At least one embodiment of this invention is presented in the drawings below and will be described in more detail herein.

SUMMARY OF THE EMBODIMENTS

Generally, the present invention and its embodiments provide for an organ retractor, namely a liver retractor, for use in laparoscopic surgeries. However, the device described herein may be suitable for any organ and any number of organs.

Preferably, the device is intended to support the liver or other organ(s) in a "hammock" type structure. A sling is formed from a suitable mesh fabric. Coupled to the mesh may be a curved needle and a straight needle. The curved needle may be attached to the diaphragm (or other suitable structure) of the patient during use and the straight needle (Keith needle) may be placed through the abdominal wall. The Keith or other suitable needle may further be anchored in position via a hemostat. The liver, being supported, by the sling will be positioned such that there is an optimal exposure of the operative field.

The sling may further be reinforced along some portion or along the entire periphery of the sling. This added rigidity allows the sling to gently cradle the liver while yet having the resiliency to properly retract the liver. The attachment points, of the suture(s) to the sling, may further be reinforced to prevent tearing during manipulation of the sling before, during, and/or after use.

In one embodiment of the present invention there is a medical device comprising: a sling; a first needle coupled to a first end of the sling, wherein the first needle is coupled via a first suture having one point of attachment on the sling; and a second needle coupled to a second end of the sling, wherein the second needle is coupled via a second suture having two points of attachment on the sling.

In another embodiment of the present invention there is a medical device comprising: a triangular sling having a reinforcement material disposed along a periphery of the sling; a curved needle coupled to the sling, via a first suture, at a first attachment point at a first end of the sling, a straight needle coupled to the sling, via a second suture, at a second attachment point and a third attachment point at a second end of the sling.

In yet another embodiment of the present invention there is a medical device comprising: a triangular, polymer sling having a silicone reinforcement material disposed along a periphery of the triangular, polymer sling, wherein the silicone reinforcement material is disposed between at least two layers of the triangular, polymer sling; a curved needle coupled to the triangular, polymer sling, via a first suture, at a first reinforced attachment point at a first end of the triangular, polymer sling; and a straight needle coupled to the triangular, polymer sling, via a second suture, at a second reinforced attachment point and a third reinforced attachment point at a second end of the triangular, polymer sling; wherein each of the first reinforced attachment point, the second reinforced attachment point, and the third reinforced attachment point are separate vertices of the triangular, polymer sling.

In general, the embodiments of the present invention succeed in conferring the following, and others not mentioned, benefits and objectives.

It is an object of the present application to provide an organ retractor that is capable of supporting a liver or other organ.

It is an object of the present application to provide an organ retractor that can be passed through a trocar during a laparoscopic procedure.

It is an object of the present application to provide an organ retractor that provides for an optimal exposure or view of the surgical area.

It is an object of the present application to provide an organ retractor that may be retained and used throughout a laparoscopic procedure.

It is an object of the present application to provide an organ retractor that will serve as a "hammock" for an organ.

It is an object of the present application to provide an organ retractor that is easy to use and requires no or limited assembly.

It is an object of the present application to provide an organ retractor that may be used for single incision laparoscopic surgery.

It is an object of the present application to provide an organ retractor that reduces the risk of hematomas and retraction injuries.

It is an object of the present application to provide an organ retractor that disperses the weight of the organ over the entire surface area of the retractor.

DESCRIPTION OF THE PREFERRED EMBODIMENTS

Figure 1:
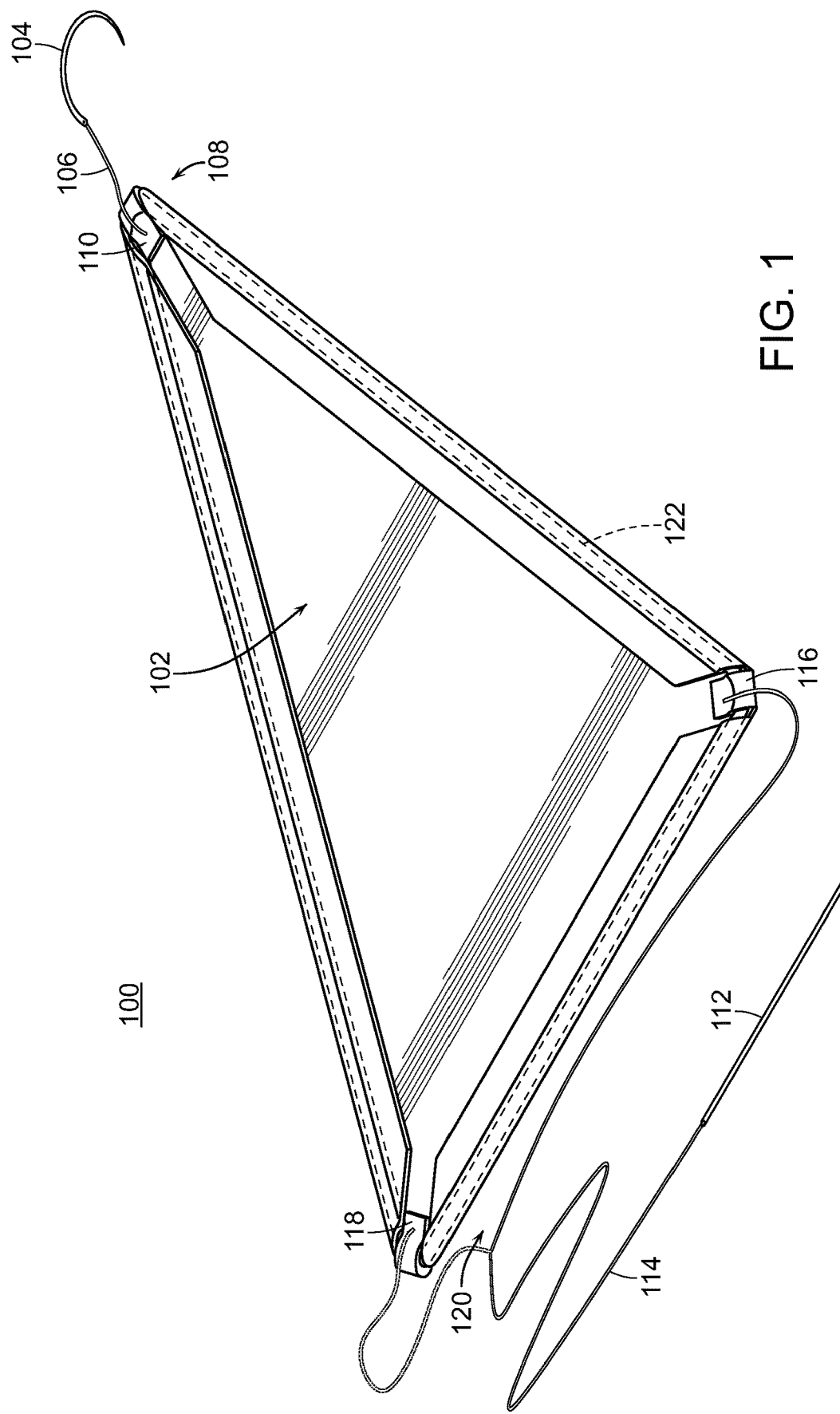
FIG. 1 is a perspective view of a first embodiment of the present invention.
Figure 2:
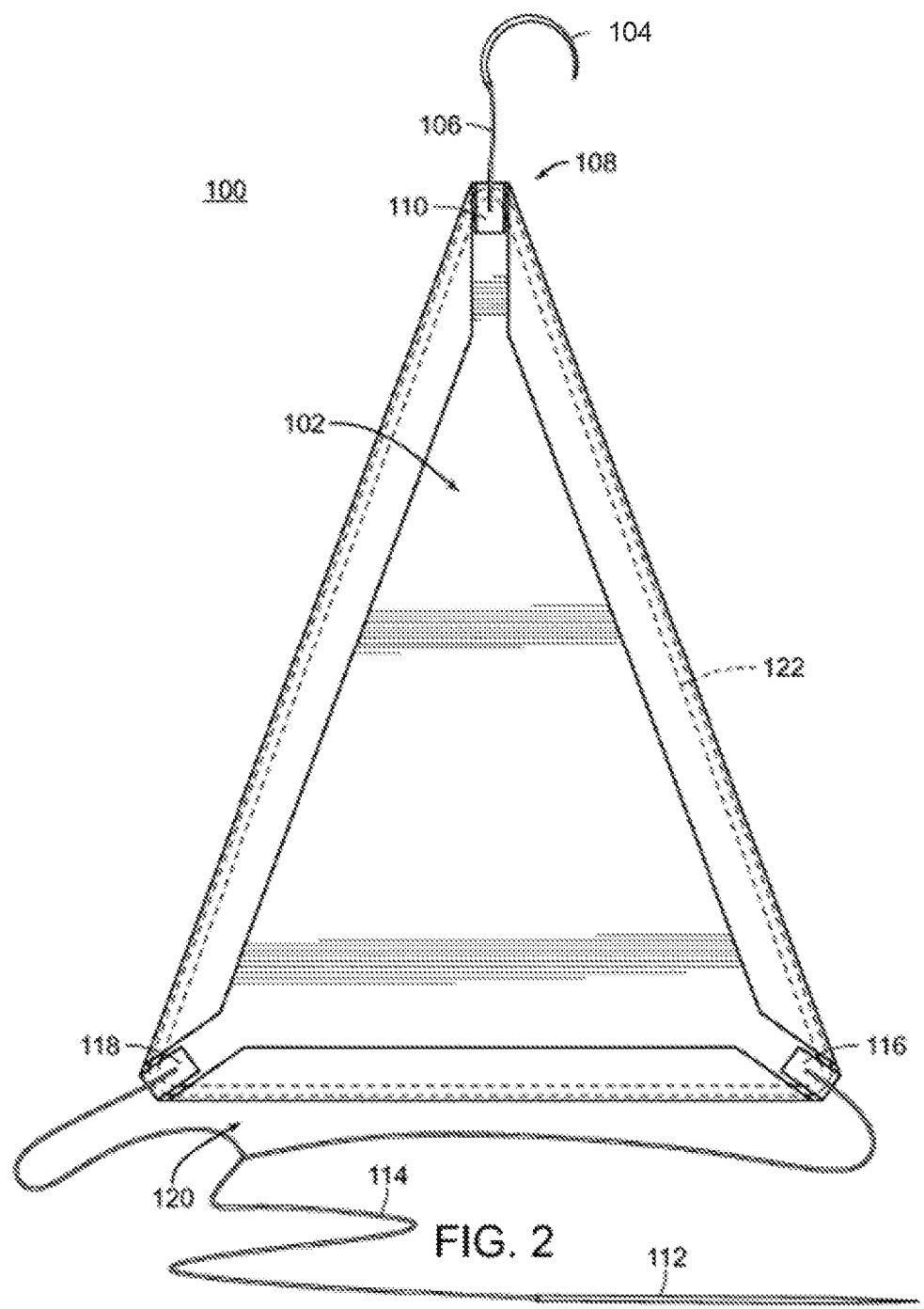
FIG. 2 is a top view of a first embodiment of the present invention.
Figure 3:
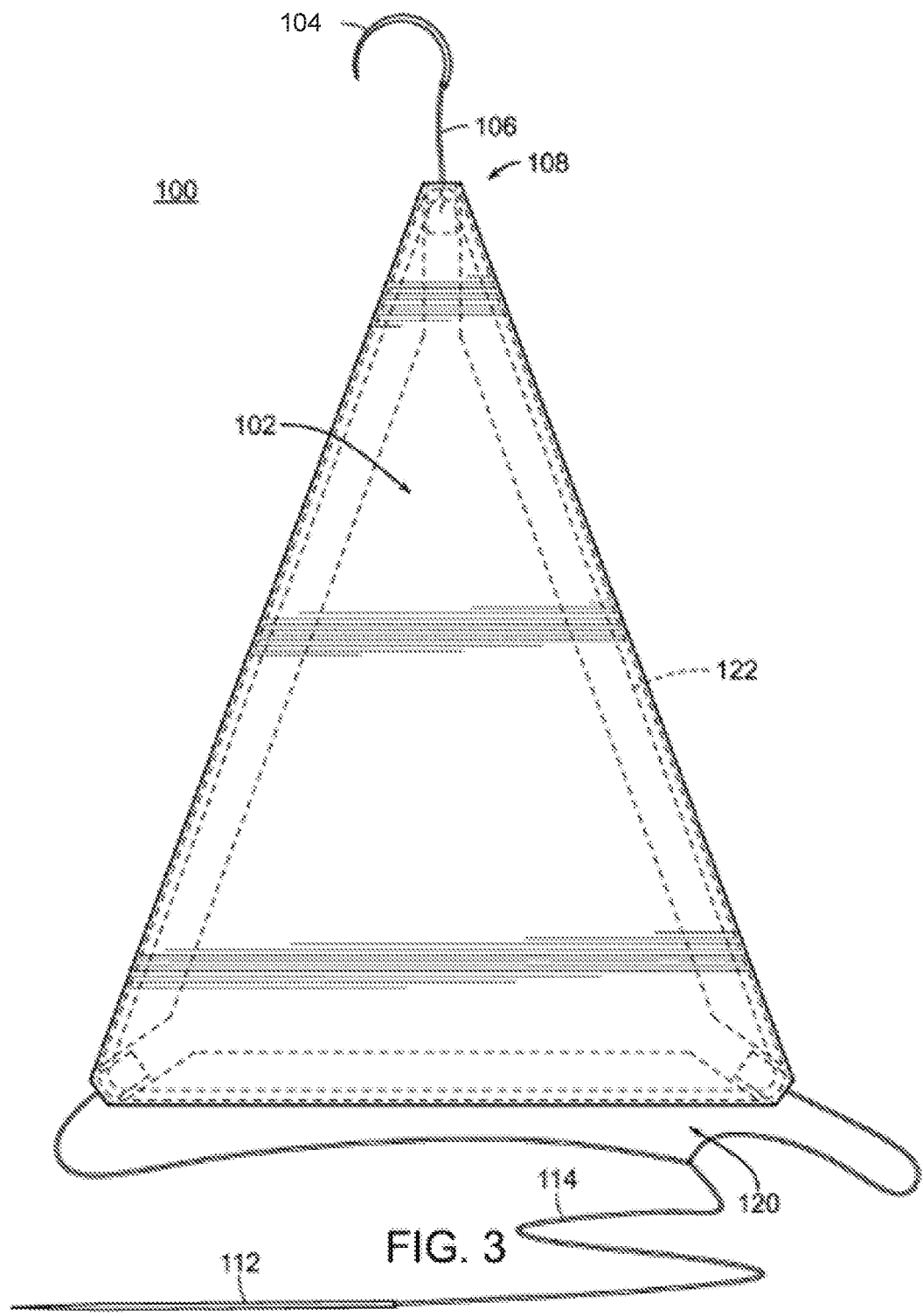
FIG. 3 is a bottom view of a first embodiment of the present invention.
Figure 4:
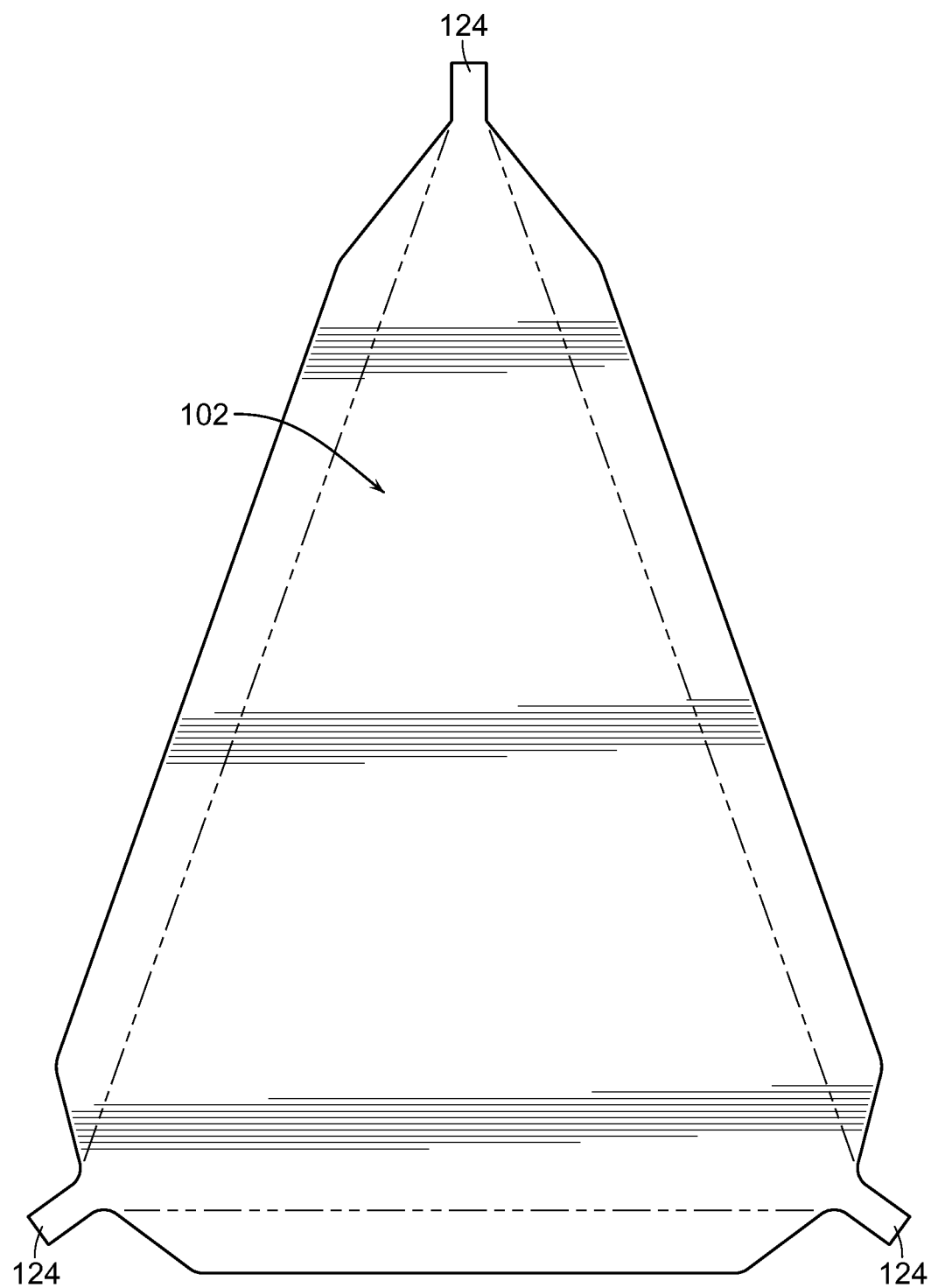
FIG. 4 is a top view of an unassembled sling of a first embodiment of the present invention.
Figure 5:
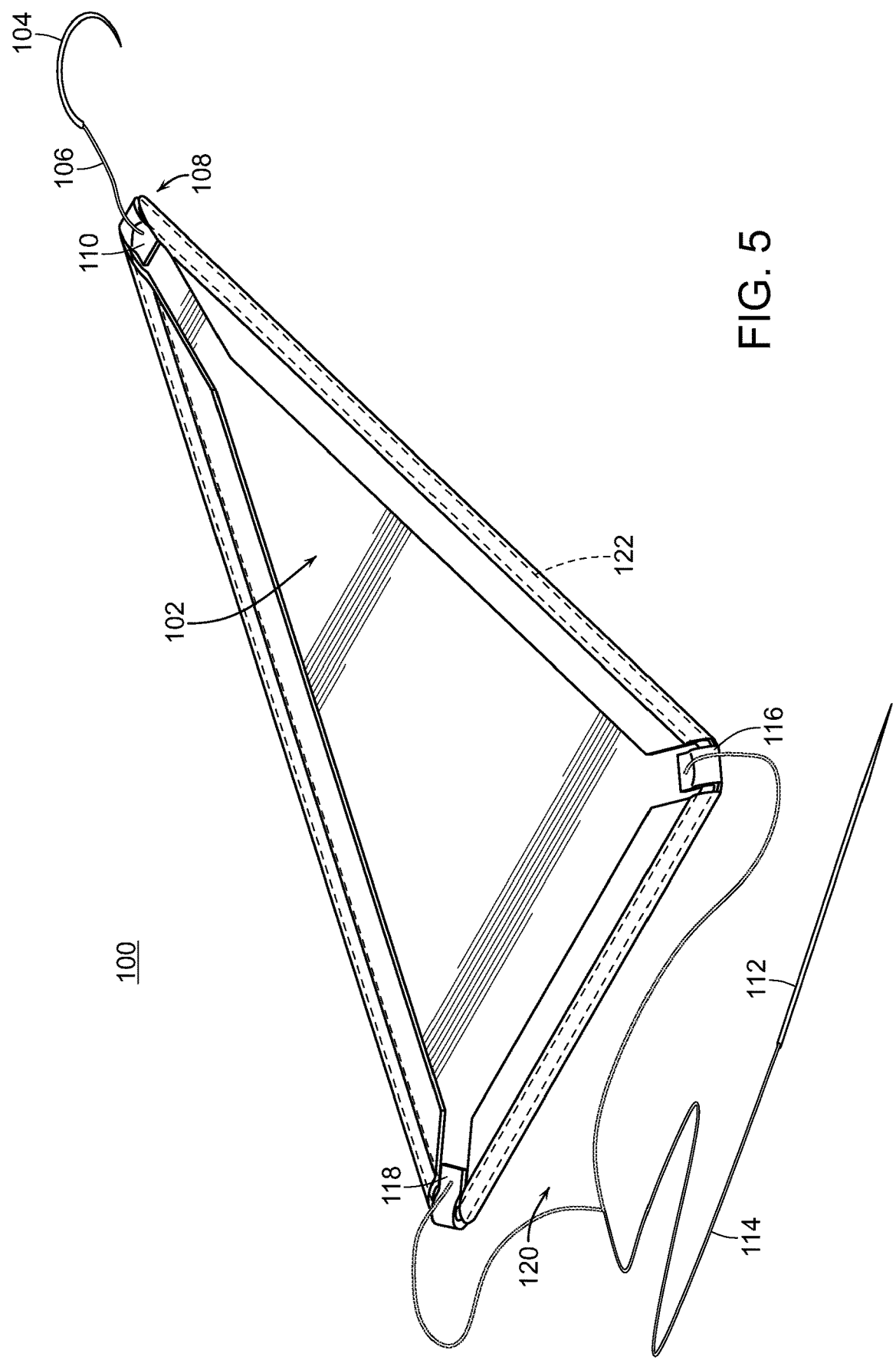
FIG. 5 is a perspective view of a second embodiment of the present invention.
Figure 6:
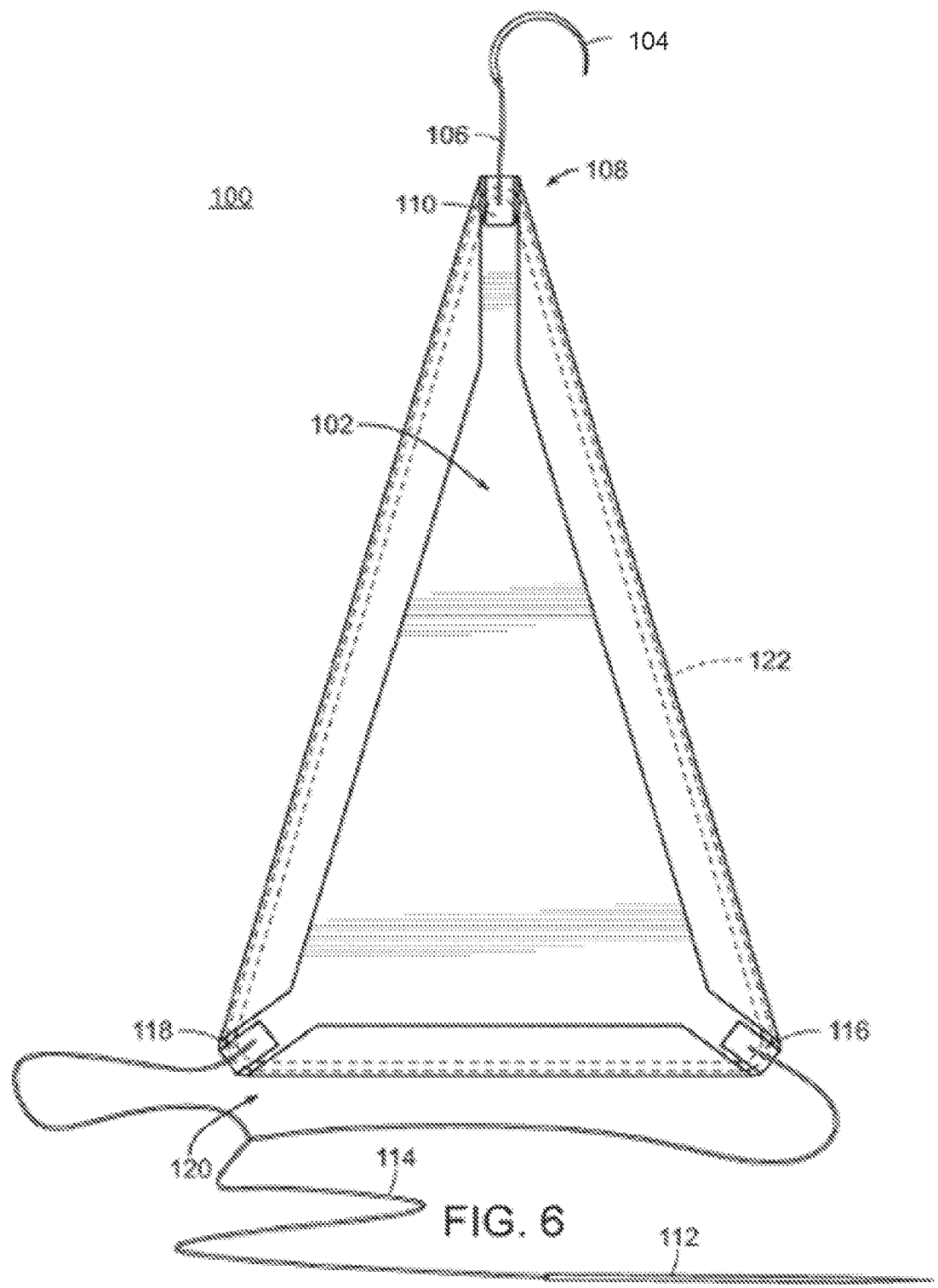
FIG. 6 is a top view of a second embodiment of the present invention.
Figure 7:
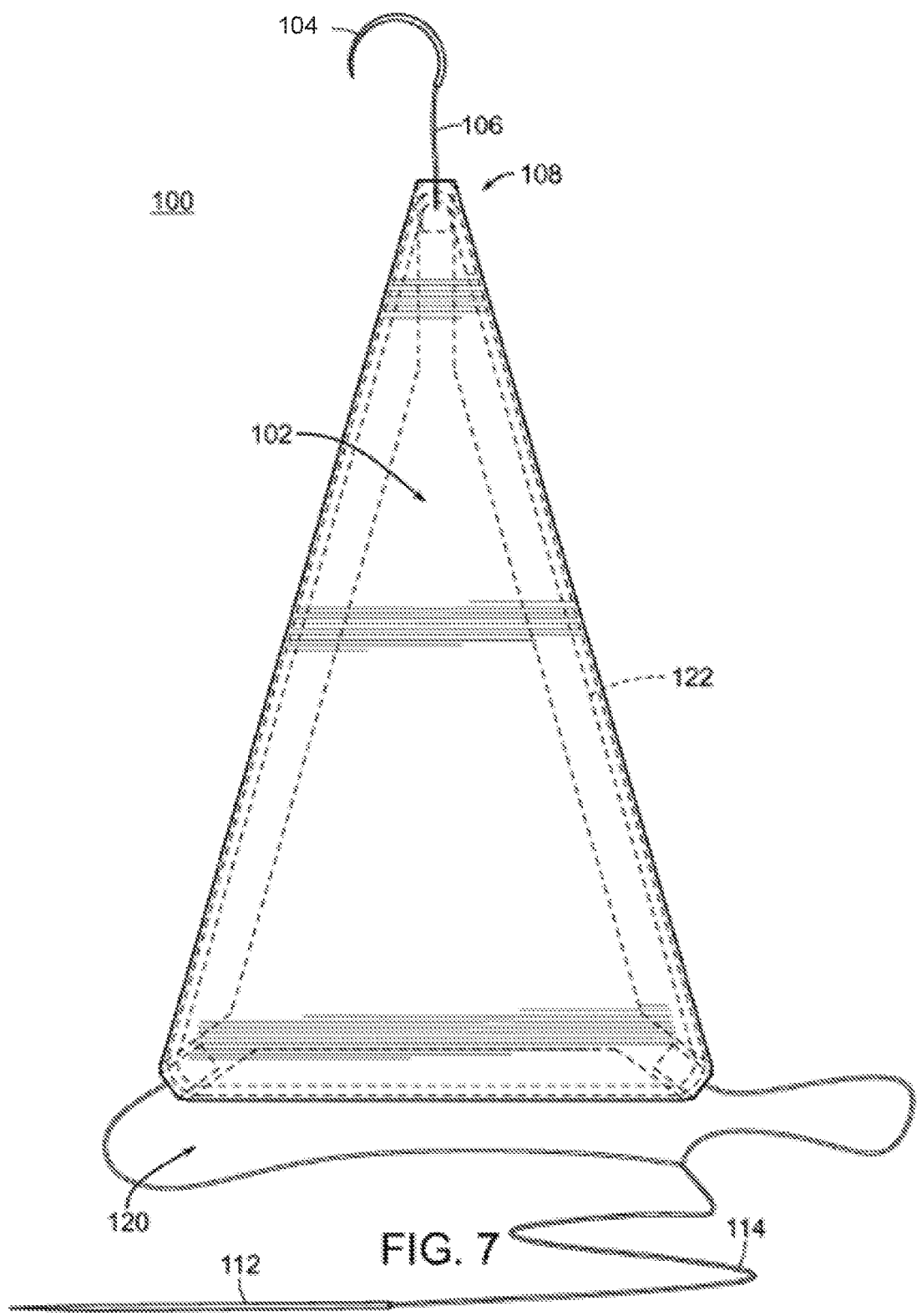
FIG. 7 is a bottom view of a second embodiment of the present invention.
Figure 8:
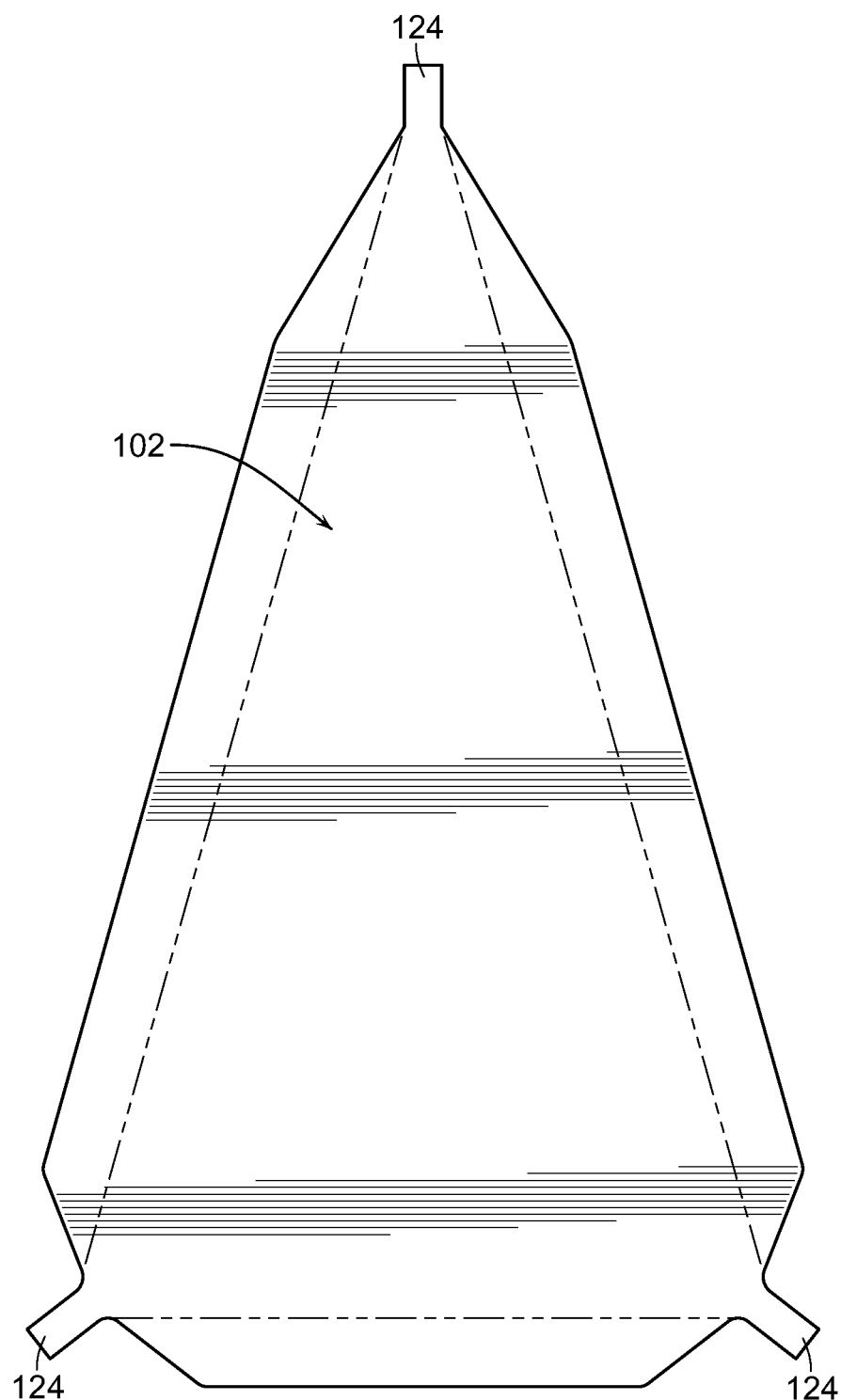
FIG. 8 is a top view of an unassembled sling of a second embodiment of the present invention.

The preferred embodiments of the present invention will now be described with reference to the drawings. Identical elements in the various figures are identified with the same reference numerals.

Reference will now be made in detail to each embodiment of the present invention. Such embodiments are provided by way of explanation of the present invention, which is not intended to be limited thereto. In fact, those of ordinary skill in the art may appreciate upon reading the present specification and viewing the present drawings that various modifications and variations can be made thereto.

Referring now to FIGS. 1-4, there is a first embodiment of the present invention. Generally, the device 100 comprises a sling 102, first needle 104, first suture 106, first attachment point 110, second needle 112, second suture 114, second attachment point 116, third attachment point 118, a reinforcement material 122, and a tab 124.

The device 100 is intended to be able to support any number and type of organs during a laparoscopic or other surgical procedure. In at least one embodiment, the device 100 is configured to support a human liver having a weight of about 1.2 kg to about 1.8 kg. In at least one embodiment, the device 100 is configured to fit into and through a 10 mm to 12 mm trocar, deploy, and subsequently be removed through the same or different 10 mm to 12 mm trocar.

The sling 102 is preferably formed from a polymer mesh fabric that is selected for its strong and flexible properties. Such a fabric may be a polypropylene knitted mesh manufactured from a 0.125 mm monofilament. In some embodiments, the fabric further has 1.0 mm by 0.6 mm pores and a weight of about 65 GSM.

The sling is generally triangular in shape, when assembled, and may take the form of an isosceles triangle. By "triangle" it is meant that the sling is a polygon having generally three main sides coming to three points or vertices. However, the points or vertices may be true vertices or may otherwise be rounded. In yet other embodiments, the triangle is a cut corner triangle where the traditional three vertices have been "cut off" thereby leaving three additional edges to the overall triangular shape as shown in the drawings.

In at least one embodiment the overall length of the finished sling is about 127 mm and may range from about 100 mm to about 150 mm. In at least one embodiment, the unassembled version of the sling has a length of about 141 mm and may range from 120 mm to about 180 mm.

The sling 102 further has a reinforcement material 122 disposed along a periphery of the sling 102. The reinforcement material 122 may be a silicone O-ring. The reinforcement material 122 is positioned and "sealed" into place by folding a portion of the sling 102 over onto itself and sealing the folded over portion using conventional means. The reinforcement material 122 allows the sling 102 and device 100, as a whole, to be inserted through a trocar and otherwise manipulated once inside the patient. Further, the reinforcement material 122 provides the necessary rigidity to support and retractor at least one organ of a patient.

At a first end 108, the sling 102 is about 5 mm in width and may range from about 1 mm to about 10 mm in width. Further at the first end 108, a first suture 106 is coupled to a first attachment point 110. The first suture 106 (and second suture 114) may be a size 0 braided surgical suture such the Vicryl® suture manufactured by Ethicon. One end of the first suture 106 is coupled to the first attachment point 110 and the second end of the first suture 106 is coupled to a first needle 104. The first needle 104 is preferably an arcuate taper pointed needle. Such a needle is capable of being coupled to the diaphragm of the patient or other structure when the device 100 is in use.

At a second end 120, the sling 102 is about 76 mm in width and may range from about 50 mm to about 100 mm. Further at the second end 120, there is a second needle 112 coupled to the sling 102 by a second suture 114. The second suture 114 preferably has multiple points of attachment to the sling 102 but the number of points of attachment may range from one to five. In a preferred embodiment, the second suture 114 is coupled on one end to the second needle 112 and coupled to the sling 102 via a second attachment point 116 and a third attachment point 118. Each of the second attachment point 116 and the third attachment point 118 are located at the vertices of the sling 102. Further, these attachment points are the vertices adjacent to the sides of the isosceles triangular shape having equal lengths.

The second needle 112 is generally a straight, cutting, surgical stainless steel needle and is more preferably a Keith-style needle. The second needle 112 is preferably about 60 mm in length but may range from about 30 mm to about 100 mm in length. In use, the second needle 112 is passed through the abdominal wall and anchored in place via a hemostat or other suitable structure. Other implementations and uses for this needles are also contained under the purview of this application.

With regard to the aforementioned first suture 106 and second suture 114, the sutures may come pre-attached or precut for use in a surgical setting. However, in other embodiments a length of suture is provided which is then cut to the specifications required by the surgical team employing the device 100.

Each of the first attachment point 110, second attachment point 116, and third attachment point 118 are openings in the sling 102 configured to allow the requisite suture to be coupled thereto. Each of the attachment points are reinforced with at least one additional layer of sling material. As shown, the sling 102 in its unassembled form, has tabs 124 located at each of the vertices. These tabs 124 are folded over onto the sling 102 and adhered thereto via conventional means such a heat sealing. This additional material strengthens the attachment points thereby providing a solid anchor for the sutures and prevents tearing or dislodgment of the sling 102 during use.

Referring now to FIGS. 5-8, there is a second embodiment of the present invention. The second embodiment is slightly narrower than the first embodiment as shown. This provides greater flexibility in terms of manner of use, but provides the same benefits as otherwise described herein.

Figure 9:
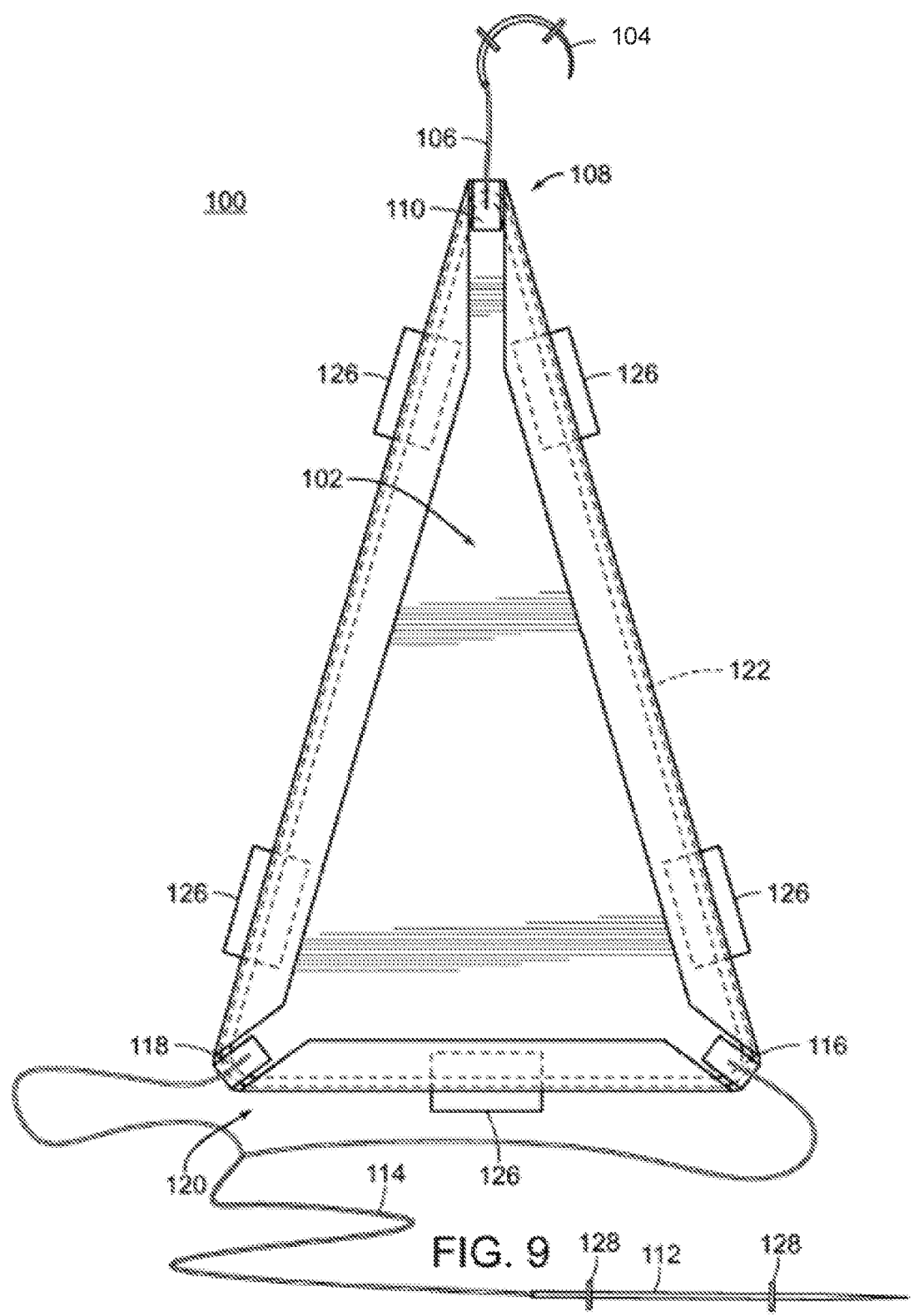
FIG. 9 is a top view of a packaging layout for an embodiment of the present invention.

In FIG. 9, there is a packaging layout for an embodiment of the present invention. Preferably, the device 100 comes fully assembled thereby allowing for "out of the box" usage by a physician. However, in other embodiments, some assembly may be required.

The sling is configured to reside in a molded pocket (not shown) with the securement tabs 126 folded or otherwise positioned to secure the sling in place. The securement tabs 126 may have an adhesive component or may have a rigidity that allows the tabs to be bent to remove the sling but otherwise are sufficiently rigid to retain the sling. There may be between two and ten securement tabs 126 and more preferably about five securement tabs 126. A portion of the securement tabs 126 is configured to be secured to the molded pocket and surrounding area, where another portion extends over the sling thereby retaining the position of the sling.

Each of the needles may be held in place by snap latches 128 which are coupled to the material forming the molded pocket. The snap latches 128 may be constructed such that the needle(s) can be pressed into a void formed by the latch arms thereby retaining the position of the needle once pressed into the latch void. To remove the needle(s), one simply need to lift up on the needle. Such an action causes the latch arms to separate thereby releasing the needle(s) from the void. Each needle is preferably held by one to five snap latches 128 and more preferably two snap latches 128 each.

Any length of suture that is coupled to the sling may have a packaging feature (not shown) allowing the suture to by properly wound around the feature to prevent tangles, knots, and the like. Posts or protrusions from the packaging material may further be used to position the suture sufficiently taut such that the device 100 may be easily unpackaged and used without having the materials tangled or otherwise rendered not useful.

Although this invention has been described with a certain degree of particularity, it is to be understood that the present disclosure has been made only by way of illustration and that numerous changes in the details of construction and arrangement of parts may be resorted to without departing from the spirit and the scope of the invention.

What is claimed is:

1. A medical device comprising:
   a triangular sling having a reinforcement material disposed along a periphery of the sling;
   a curved needle coupled to the sling, via a first suture, at a first attachment point at a first end of the sling; and
   a straight needle coupled to the sling, via a second suture, at a second attachment point and a third attachment point at a second end of the sling, such that the second suture, the second attachment point, and the third attachment point form a triangular guyline,
   wherein each of the first attachment point, second attachment point, and third attachment point are located at a vertex of the triangular sling, and
   wherein each the first attachment point, second attachment point, and third attachment point are at a separate vertex.

2. The device of claim 1 wherein the first suture and the second suture are braided sutures.

3. The device of claim 1 wherein each vertex of the triangular sling is reinforced.

4. The device of claim 1 wherein each vertex of the triangular sling has a portion forming the triangular sling folded over and adhered thereto.

5. The device of claim 1 wherein a length of the sling is about 127 mm.

6. A medical device comprising:
   a triangular, polymer sling having a silicone reinforcement material disposed along a periphery of the triangular, polymer sling,
      wherein the silicone reinforcement material is disposed between at least two layers of the triangular, polymer sling;
   a curved needle coupled to the triangular, polymer sling, via a first suture, at a first reinforced attachment point at a first end of the triangular, polymer sling; and
   a straight needle coupled to the triangular, polymer sling, via a second suture, at a second reinforced attachment point and a third reinforced attachment point at a second end of the triangular, polymer sling;
   wherein each of the first reinforced attachment point, the second reinforced attachment point, and the third reinforced attachment point are separate vertices of the triangular, polymer sling.

7. The device of claim 6 wherein the triangular, polymer sling forms an isosceles triangle.

8. The device of claim 7 wherein the second reinforced attachment point and the third reinforced attachment point are vertices of the isosceles triangle adjacent to each of the two equal length sides of the isosceles triangle.

9. The device of claim 6 wherein the triangular, polymer sling has pores comprising dimensions of about 1.0 mm by about 0.6 mm.

* * * * *